(12) United States Patent
Yamaguchi

(10) Patent No.: US 10,280,448 B2
(45) Date of Patent: May 7, 2019

(54) NUCLEIC ACID DENATURATION APPARATUS, METHOD FOR DENATURING NUCLEIC ACID AND METHOD FOR AMPLIFYING NUCLEIC ACID

(71) Applicant: KANAGAWA UNIVERSITY, Yokohama-Shi (JP)

(72) Inventor: Shigeo Yamaguchi, Yokohama (JP)

(73) Assignee: KANAGAWA UNIVERSITY, Yokohama-Shi (JP)

( * ) Notice: Subject to any disclaimer, the term of this patent is extended or adjusted under 35 U.S.C. 154(b) by 0 days.

(21) Appl. No.: 14/423,596

(22) PCT Filed: Aug. 28, 2013

(86) PCT No.: PCT/JP2013/073039
§ 371 (c)(1),
(2) Date: Feb. 24, 2015

(87) PCT Pub. No.: WO2014/034732
PCT Pub. Date: Mar. 6, 2014

(65) Prior Publication Data
US 2015/0322484 A1    Nov. 12, 2015

(30) Foreign Application Priority Data
Aug. 30, 2012    (JP) ................. 2012-189441

(51) Int. Cl.
*C12Q 1/68* (2018.01)
*C12Q 1/6806* (2018.01)
(Continued)

(52) U.S. Cl.
CPC .............. *C12Q 1/6806* (2013.01); *B01L 9/06* (2013.01); *C12Q 1/686* (2013.01); *B01L 7/52* (2013.01); *B01L 2400/0433* (2013.01)

(58) Field of Classification Search
CPC ........ C12Q 2523/301; C12Q 2523/305; C12Q 1/6806; B01L 2400/0433; B01L 9/06; B01L 2400/0439
See application file for complete search history.

(56) References Cited

U.S. PATENT DOCUMENTS 6,071,480 A *  6/2000  Halaka ................ B01F 11/0266
                                                        422/128
8,169,122 B1 *  5/2012  Roberts .................. C12N 13/00
                                                        310/322
(Continued)

FOREIGN PATENT DOCUMENTS

WO        2006124725 A2     11/2006
WO     WO-2008057375 A2      5/2008
WO     WO-20210138800 A1    12/2010

OTHER PUBLICATIONS

International Preliminary Report on Patentability dated Mar. 12, 2015.

(Continued)

*Primary Examiner* — Betty J Forman
(74) *Attorney, Agent, or Firm* — Nixon Peabody LLP; Thomas P. Pavelko

(57) ABSTRACT

[Problem] To provide an apparatus for denaturing double strand nucleic acids to single strand nucleic acids, and a method for denaturing double strand nucleic acids to single strand nucleic acids, which may become an alternative means to the thermal denaturation.
[Solution] A nucleic acid denaturation apparatus 100 according to the present invention is provided with a vibration generation part 10 for generating vibration to be given to a nucleic acid solution containing double strand nucleic acids, which gives the vibration that occurs in the vibration generation part to the nucleic acid solution, thereby denaturing (Continued)

the double strand nucleic acids in the nucleic acid solution to single strand nucleic acids.

10 Claims, 6 Drawing Sheets

Specification includes a Sequence Listing.

(51) Int. Cl.
   *C12Q 1/686* (2018.01)
   *B01L 9/06* (2006.01)
   *B01L 7/00* (2006.01)

(56) References Cited

U.S. PATENT DOCUMENTS

| | | | |
|---|---|---|---|
| 2002/0009015 A1* | 1/2002 | Laugharn, Jr. | B01F 11/02 366/108 |
| 2004/0197806 A1* | 10/2004 | Yoshida | G01N 33/54373 435/6.11 |
| 2006/0270022 A1* | 11/2006 | Bickmore, Jr. | B01L 7/52 435/287.2 |
| 2010/0112567 A1 | 5/2010 | Adolfsen et al. | |
| 2011/0130560 A1 | 6/2011 | Sadri et al. | |

OTHER PUBLICATIONS

International Search Report dated Nov. 19, 2013.
Sokoloff, J. B., "Damping and softening of low frequency vibrational modes of long molecules when placed in a viscous solvent", The Journal of Chemical Physics, 1988, vol. 89, No. 4, pp. 2330-2335.
European Patent Office Action for Application No. 13 832 105.4-1404, dated Apr. 4, 2017.
English Translated Notification of Reasons for Refusal for Application No. 2014-533050, 3 pages.
Webpage entitled, "UNIMAG ZX3," www.uniequip.com/en/pdf/UNIMAG_ZX.pdf 1 page.
Liner Gallisendorfer, entitled, "Generation and Characterization of Liver Cancer-Derived Growth Factor (HDGF) Deficient Mouse Model;" dated Mar. 2011, http://hss.ulb.uni-bonn.de/diss_online, 32 pages.
The Journal of Chemical Physics, J.B. Sokoloff, entitled, "Damping and Softening of Low Frequency Vibrational Modes of Long Molecules When Placed in a Viscous Solvent," dated Aug. 15, 1988, vol. 89, 8 pages.
European Office Action for Application No. 13832105.4 dated Mar. 4, 2018.

* cited by examiner

NUCLEIC ACID DENATURATION APPARATUS, METHOD FOR DENATURING NUCLEIC ACID AND METHOD FOR AMPLIFYING NUCLEIC ACID

CROSS-REFERENCE TO RELATED APPLICATIONS

This application is a National Phase filing under 35 U.S.C. § 371 of PCT/JP2013/073039 filed on Aug. 28, 2013, which claims priority of Japanese Patent. Application Serial No. 2012-189441 filed on Aug. 30, 2012, the entire contents of which are hereby incorporated by reference in their entireties

TECHNICAL FIELD

The present invention relates to a nucleic acid denaturation apparatus, a method for denaturing nucleic acids and a method for amplifying nucleic acids.

BACKGROUND ART

For a polymerase chain reaction (PCR) or the like, it is required to denature double strands of DNA or the like prepared from a sample to single strands. Conventionally, as a method for denaturing double strand nucleic acids to single strand nucleic acids, thermal denaturation has been mainly used which utilizes the property of the hydrogen bonding between the nucleic acid bases of a double strand nucleic acid of being cut by heat.

For example, the typical thermal denaturation in a PCR method adds heat to a sample including a DNA at approximately 90 to 95° C. and dissociates the double strand nucleic acids to single strand nucleic acids. Subsequently, in the annealing step, the sample is cooled to approximately 50 to 65° C. so as to anneal with a primer that is complementary to the DNA, and in the elongation step, the sample is heated to approximately 70 to 72° C. to elongate, starting from the primer, a strand that is complementary to the single strand with the use of a polymerase (e.g., refer to WO 2008/057375 A (JP-2010-508813 A)). These steps are typically repeated 25 to 40 times.

Therefore, it is necessary for the activity of a DNA polymerase used for a PCR to be maintained in the thermal cycles, in particular in a high temperature range from 90 to 95° C.

Alternatively, it is also conventionally carried out to denature double strands of DNA to single strands with alkali. This utilizes the property of double strands of DNA of dissociating and denaturing to single strands in an environment having a pH of 10 or more.

SUMMARY OF INVENTION

Technical Problem

In a case of thermal denaturation, it is necessary to use a heat-resistant polymerase which may survive the thermal denaturation as described above, and it is a problem that the usable enzyme is limited. For example, a Taq polymerase typically used for a PCR has so high optimum temperature as to survive the thermal denaturation cycles, but has so low exonuclease activity that the probability of taking in a wrong nucleotide is slightly high. In addition, a temperature at which denaturation occurs varies depending on the base composition and the length (the number of bases) of DNA. In other words, a higher temperature may be required as the DNA is longer. In addition, it becomes problem that the Taq polymerase is very expensive.

In addition, in a case of alkali denaturation, for example, the polymerase or the like used for a PCR method may not be added at the time of alkali denaturation, and in each step, it is necessary to add an alkali denaturation liquid, a neutralization liquid and a DNA polymerase. Therefore, manipulation becomes so complicated that it is difficult to amplify various kinds of samples in parallel with PCR.

Accordingly, it is considered that providing a technique, in place of the thermal denaturation which has the necessity to add high temperature heat or the alkali denaturation which makes the environment severe, markedly widens the choice of enzyme, for example polymerase.

Accordingly, it is an object of the present invention to provide a nucleic acid denaturation apparatus for denaturing double strand nucleic acids to single strand nucleic acids, a method for denaturing nucleic acids, and a method for amplifying nucleic acids, which may become an alternative means to the thermal denaturation.

Means for Solving Problem

A nucleic acid denaturation apparatus according to the present invention to achieve the object above includes a vibration generation part for generating vibration to be given to a nucleic acid solution containing double strand nucleic acids, has a feature of denaturing the double strand nucleic acids in the nucleic acid solution to single strand nucleic acids by giving the vibration that occurs in the vibration generation part to the nucleic acid solution.

In addition, a method for denaturing nucleic acids according to the present invention includes a step of giving vibration that occurs in a vibration generation part to a nucleic acid solution containing double strand nucleic acids, thereby denaturing the double strand nucleic acid in the nucleic acid solution to single strand nucleic acids. Furthermore, a method for amplifying nucleic acids according to the present invention includes a step of obtaining single strand nucleic acids by the above described method for denaturing nucleic acids, and a step of amplifying double strand nucleic acids with the use of the single strand nucleic acids.

DESCRIPTION OF EMBODIMENTS

A nucleic acid denaturation apparatus according to the present invention includes a vibration generation part for generating vibration to be given to a nucleic acid solution containing double strand nucleic acids, has a feature of denaturing the double strand nucleic acids in the nucleic acid solution to single strand nucleic acids by giving the vibration that occurs in the vibration generation part to the nucleic acid solution.

In addition, a method for denaturing nucleic acids according to the present invention includes a step of giving vibration that occurs in a vibration generation part to a nucleic acid solution containing double strand nucleic acids, thereby denaturing the double strand nucleic acids in the nucleic acid solution to single strand nucleic acids. Furthermore, a method for amplifying a nucleic acid according to the present invention includes a step of obtaining single strand nucleic acids by the above described method for denaturing nucleic acids, and a step of amplifying double strand nucleic acids with the use of the single strand nucleic acids.

In the nucleic acid denaturation apparatus and the method for denaturing nucleic acids according to the present invention, giving the vibration that occurs in the vibration generation part to a nucleic acid solution containing double strand nucleic acids allows the double strand nucleic acids in the nucleic acid solution to denature to single strand nucleic acids. As such, the vibration may trigger the double strand nucleic acids to denature to single strand nucleic acids, and thus addition of heat is not required. Accordingly, an extremely simple and easy method called vibration may denature double strand nucleic acids to single strand nucleic acids.

Hereinafter, with reference to the attached drawings, a description is made of embodiments of the present invention. Note that the following description does not limit the technical scope nor the meaning of the term recited in the claims. In addition, the dimension ratio of the drawings is overstated on account of the description, and thus may be different from the real ratio.

Figure 1:
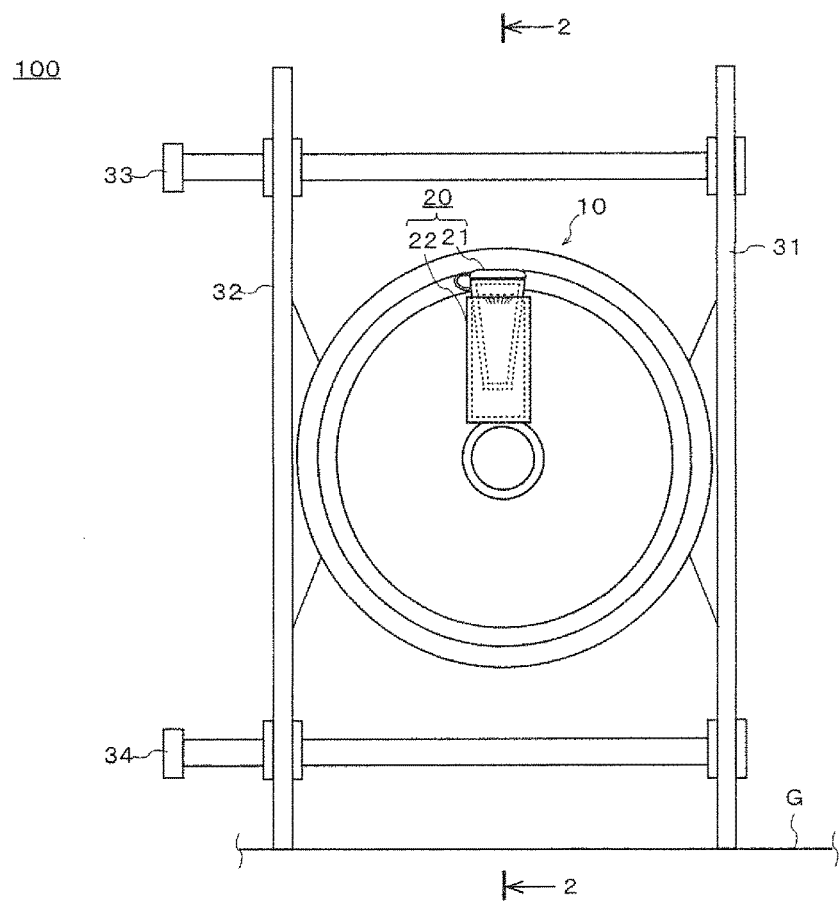
FIG. 1 is a front elevational view showing a nucleic acid denaturation apparatus according to an embodiment of the present invention.
Figure 2:
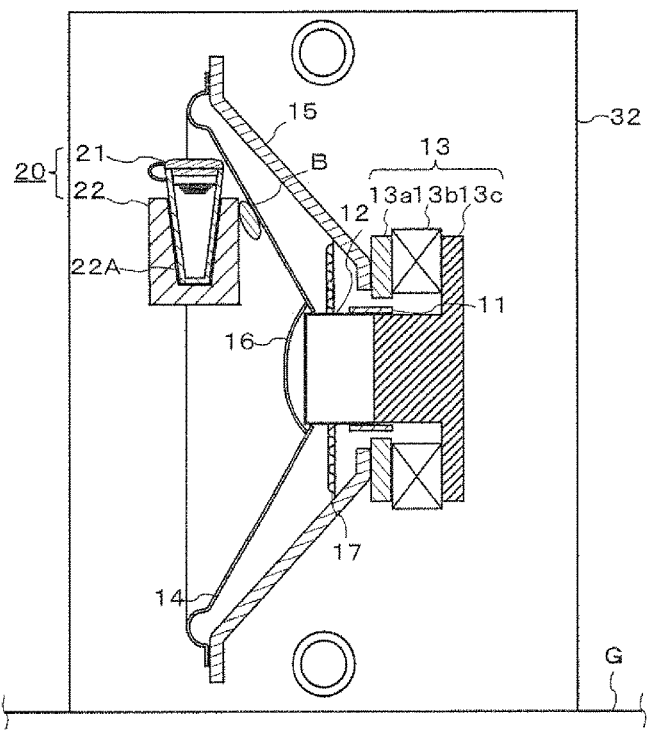
FIG. 2 is a cross sectional view along the 2-2 line in FIG. 1.

FIG. 1 is a front elevational view showing the nucleic acid denaturation apparatus according to an embodiment of the present invention, and FIG. 2 is a cross sectional view along the 2-2 line in FIG. 1.

Giving an outline with reference to FIG. 1 and FIG. 2, the nucleic acid denaturation apparatus 100 according to this embodiment is provided with a vibration generation part 10 for generating vibration to be given to a nucleic acid solution containing double strand nucleic acids. The nucleic acid denaturation apparatus 100 gives the vibration that occurs in the vibration generation part 10 to the nucleic acid solution, thereby denaturing the double strand nucleic acids in the nucleic acid solution to single strand nucleic acids.

In addition, in this embodiment, the nucleic acid denaturation apparatus 100 is provided with a nucleic acid solution reception part 20 for receiving a nucleic acid solution. The nucleic acid solution reception part 20 is provided with a container 21 and a container retainer member 22. A nucleic acid solution is received in the container 21, and the container 21 is retained by the container retainer member 22.

The container retainer member 22 is connected to the vibration generation part 10 with an adhesive B. Therefore, the vibration generation part 10 is connected to a nucleic acid solution through the container 21 and the container retainer member 22. Note that in the present invention, a case is also included where the nucleic acid solution reception part 20 is provided only with the container 21 but does not include the container retainer member 22. In other words, an embodiment is also included where the vibration generation part 10 is connected to a nucleic acid solution only through the container 21 but not through the container retainer member 22. In this embodiment, giving the vibration that occurs in the vibration generation part 10 to a nucleic acid solution received in the container 21 supported by the container retainer member 22 allows the double strand nucleic acids in the nucleic acid solution to denature to single strand nucleic acids.

In this embodiment, connecting a nucleic acid solution to the vibration generation part 10 through the container 21 and the container retainer member 22 in use allows the nucleic acid solution itself to vibrate through the container 21 and the container retainer member 22. In this way, adding the vibration to a nucleic acid solution itself may vibrate the whole fluid, thereby effectively denaturing the double strand nucleic acids to single strand nucleic acids. Hereinafter, a detailed description is made.

The vibration generation part 10 is provided with a voice coil 11 for generating vibration in a speaker in this embodiment, a voice coil bobbin 12 around which the voice coil 11 is wound, a damper 17 for supporting the voice coil bobbin 12, a magnetic circuit 13 for giving driving force to the voice coil 11, a vibration board 14 for receiving the vibration by the voice coil 11 to vibrate, and a frame 15 for supporting the peripheral part of the vibration board 14.

The voice coil 11 is provided at the upstream side in the transmission direction of the vibration by the vibration board 14. The voice coil 11 is wound around the voice coil bobbin 12. The end part of the voice coil bobbin 12 is covered with a cap 16. The damper 17, which is located at the outside in the radial direction of the voice coil bobbin 12, supports the voice coil bobbin 12.

The vibration board 14 is directly connected to the voice coil bobbin 12. Therefore, the vibration board 14 receives the vibration from the voice coil 11, and then vibrates along with the voice coil 11 through the voice coil bobbin 12. The vibration board 14 is located so as to face in the horizontal direction with respect to the ground G.

The magnetic circuit 13 is provided with a plate 13A, a magnet 13B and a yoke 13C. The plate 13A is fixed to the frame 15. The magnet 13B is held by the plate 13A and the yoke 130. A magnetic field is formed by the magnetic circuit 10 having such a composition, in which giving a sound current to the voice coil 11 allows the voice coil 11 to vibrate, so that the vibration board 14 connected to the voice coil 11 vibrates. The material, the thickness or the like of the vibration board 14 may be determined in view of the container 21 for use, the amount of a nucleic acid solution or the like.

The vibration generation part 10 is sandwiched between plastic boards 31, 32 in the horizontal direction, as shown in FIG. 1. The vibration generation part 10 in a state of being sandwiched between the plastic boards 31, 32 does not have an obstacle in the vibration direction of the vibration generation part 10, and is maintained at a fixed distance away from the ground G so that the vibration from the vibration generation part 10 is not disturbed as far as possible. The plastic boards 31, 32 are fixed in a state of inserting the vibration generation part 10 therebetween by a fastening means such as bolts 33, 34.

The vibration generation part 10 generates a vibration having a frequency in the audible range with the use of the vibration board 14 for use with a speaker or the like. The vibration generated from the vibration generation part 10 may be appropriately set in accordance with the shape or the size of the container 21, the property of double strand nucleic acids to be denatured, or the like, but is preferably in the audible range, more preferably from 20 to 20,000 Hz, more preferably from 50 to 2,000 Hz.

Adding a vibration in this range allows a double strand to effectively denature to single strands, along with makes it unnecessary to concern about the damage to a DNA due to a vibration having a high frequency. The above described vibration in the audible range has a higher frequency than, for example, that for stirring a solution with a stirrer, while having a lower frequency than that of the ultrasound. Note that in the above described embodiment, a speaker is used for generating a vibration having a frequency in the audible range, but another vibration generating source, for example a piezoelectric vibrator may also be used, as long as it is a vibration source for generating a vibration in the audible range.

Figure 3:
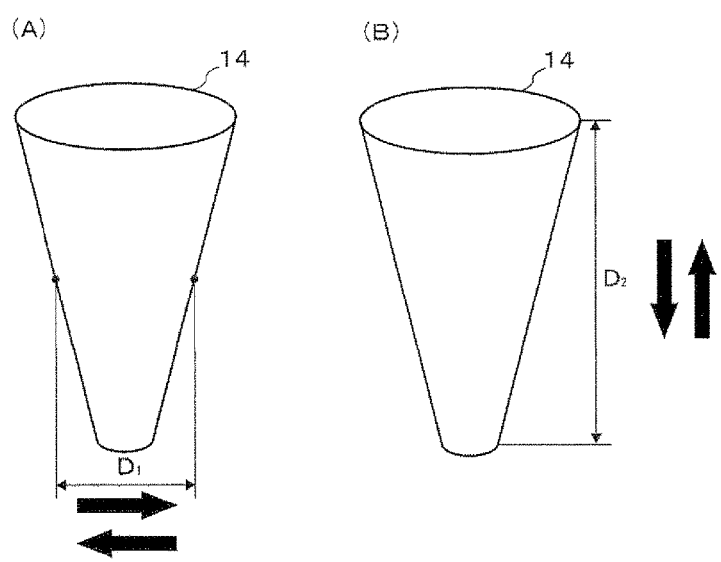
FIGS. 3(A) and 3(B) are explanatory views for illustrating the amplitude of vibration that occurs in a vibration generation part.

FIGS. 3(A) and 3(B) are explanatory views for illustrating the amplitude of the vibration that occurs in the vibration generation part. The amplitude of the vibration that occurs in the above described vibration generation part may be appropriately set in accordance with the shape of the container for receiving a nucleic acid solution or the like. As to an example of the amplitude of vibration, assuming that, as shown in FIG. 3(A), the diameter in the center portion of the vibration board 14 when the vibration occurs so as to be perpendicular to the axis of the circular truncated cone shape of the vibration board 14 is $D_1$, and as shown in FIG. 3(B), the distance from one end part to the other end part in the axial direction of the vibration board 14 when the vibration occurs in the direction of the axis of the vibration board 14 is $D_2$, the range of the amplitude is preferably from ($D_1$ or $D_2$)/10000 to 10×($D_1$ or $D_2$).

The nucleic acid for use in this embodiment is a DNA, but the nucleic acid is not 1 invited in particular, so a variety of nucleic acids may be used. A specific example of the nucleic acid may include a DNA, RNA, PNA, oligodeoxyribonucleotide, oligoribonucleotide or the like, or a chemically modified nucleic acid of the above described nucleic acid. An example of the chemically modified nucleic acid may include a 2'-O-methyl (Me) RNA or the like. An example of the double strand nucleic acid specifically includes a combination of a DNA and a DNA; a combination of an RNA and an RNA or the like, but a combination of a DNA and a DNA is preferable.

As a method for preparing double strand nucleic acids, a conventionally publicly known method may be used, and the double strand nucleic acid is produced from a living body sample such as blood or a cell of a human being, food, or an environmental sample such as soil, river water or seawater. As a method for extracting double strand nucleic acids from these samples, for example, a commercially available kit for DNA extraction or the like may be used.

Because the concentration of double strand nucleic acids in solution depends on the sensitivity of detection of a detection technique or a sensing device, the concentration may be determined by the specification or a preliminary examination. In one preferable embodiment, the concentration is from 1 ng per ml of sample to 1 mg/mL.

Because a nucleic acid solution may be scattered by the vibration, it is desirable that the container 21 in which the nucleic acid solution is received be a container having a lid. The container is not limited in particular, and an example thereof includes around 0.1 to 2.0 ml microtubes. The material thereof may include plastic or glass, preferably polypropylene or polyethylene. In addition, it is preferable that the volume of the microtube be around 0.1 to 2.0 ml. In addition, the shape of the microtube may specifically include the one of an ASSIST tube made by ASSIST, or the one of an Eppendorf tube made by Eppendorf, but the shape of the microtube product sold from another company under almost the same standard may also be used.

The container retainer member 22 is a member for retaining and fixing onto the nucleic acid denaturation apparatus the container 21 for receiving a nucleic acid solution containing double strand nucleic acids. In this embodiment, copper is used for the container retainer member 22, but the material is not limited thereto as long as it may support the container 21.

In addition, the container retainer member 22 is provided with a reception part 22A that is formed to correspond to the appearance shape of the container 21, with the use of which only placing the container 21 on the container retainer member 22 allows the container 21 to be retained by the container retainer member 22, so that the container 21 may be easily attached and detached. In this way, without taking out from the container 21 a nucleic acid solution after double strand nucleic acids is denatured, the next denaturation process may be carried out only by taking out from the container retainer member 22 the whole container in which the nucleic acid solution is received, and by placing another container in which a nucleic acid solution is received. Accordingly, the denaturing process may be easily carried out.

In addition, the reception part 22A of the container retainer member 22 may be provided with a slip stopper such as rubber. When the container retainer member 22 is provided with a slip stopper member in this way, the container 21 is so strongly fixed that, even in a case where the container 21 receives such a vibration as having a magnitude of causing the container 21 to be detached from the container retainer member 22, the container 21 is not easy to be detached from the container retainer member 22 by friction. Accordingly, a situation where vibration is so large that the container is detached from the container retainer member 22 and thus the vibration is not transmitted to a nucleic acid solution, or a situation where vibration causes a nucleic acid solution in the container to leak may be prevented.

In addition, in this embodiment, one container 21 is placed in the container retainer member 22, but a plurality of containers 21 may also be placed. Placing a plurality of containers 21 allows a plurality of samples to denature at one time.

Figure 4:
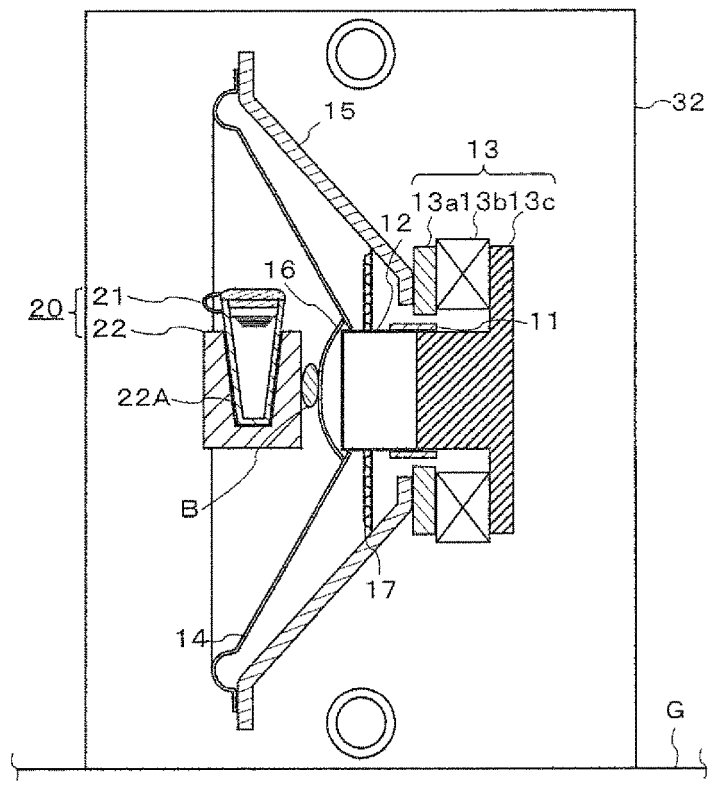
FIG. 4 is a cross sectional view of the same position as that of FIG. 2, showing a modified example of the present invention.

FIG. 4 is a cross sectional view of the same position as that of FIG. 2, showing a modified example as to the connection of the vibration generation part to the container retainer member. In FIG. 2, the container retainer member 22 is connected with the adhesive B to the inclined portion that is the peripheral portion of the vibration board 14, but as long as the vibration may be transmitted to a nucleic acid solution in the container, the container retainer member 22 may also be connected to the portion of the cap 16 that is the center portion of the vibration generation part 10 as shown in FIG. 4.

Figure 5:
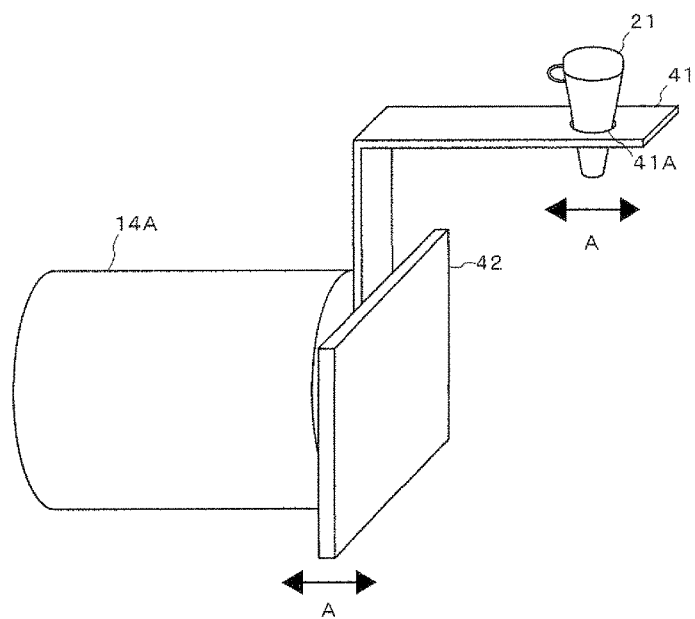
FIG. 5 is a perspective view showing a nucleic acid denaturation apparatus according to a modified example of the present invention.

FIG. 5 is a perspective view showing the nucleic acid denaturation apparatus according to a modified example of the present invention. The container retainer member 22 also has the function as a vibration transmission member for transmitting the vibration from the vibration generation part 10 between the vibration generation part 10 and the container 21. The composition of the vibration transmission member other than the container retainer member 22 includes, for example, an L-shaped support board 41 that is fixed to a vibrator 14A by a fixing board 42 and that is provided with a container insertion hole 41A through which the container 21 is insertable as shown in FIG. 5.

The vibration in the horizontal direction A as shown in FIG. 5 that occurs in the vibrator 14A is also transmitted to the container 21 through the support board 41, which promotes the denaturation of a nucleic acid solution in the container 21. When the vibration transmission member is composed in this way, even in a case where it is difficult to directly connect the container 21 to the vibration generation part 10, the vibration may be transmitted to a nucleic acid solution in the container 21 through the vibration transmission member. Accordingly, the denaturation process may be carried out even without preparing an exclusive container for denaturation of double strand nucleic acids or the like.

In the above described embodiment, a description is made of the nucleic acid denaturation apparatus 100 provided with the container retainer member 22 and the adhesive B, but as long as the apparatus 100 is an apparatus which is provided with the vibration generation part, and which has a denaturing effect on double strand nucleic acids to single strand nucleic acids by the vibration generated by the above described vibration generation part, the present invention includes any other form. For example, with the use of an adhesive member (for example, an adhesive), the container may also be directly connected to the vibration generation part in use.

Next, a description is made of a method for denaturing double strand nucleic acids with the use of the nucleic acid denaturation apparatus 100 according to this embodiment. First of all, placing and fixing the container 21 in which a nucleic acid solution is received into the container retainer member 22 are performed. Subsequently, sending a sound current to the voice coil 11 of the vibration generation part 10, thereby vibrating the voice coil 11 to vibrate the vibration board 14 are performed. The container retainer member 22 is connected to the vibration board 14 with the adhesive B, and thus the container retainer member 22 receives the vibration from the vibration board 14 so as to vibrate, thereby further vibrating the container 21 fixed to the container retainer member 22, with the result that the vibration is transmitted to a nucleic acid solution in the container.

As a result of intensive research, the inventor has found that a quite simple and easy method including not adding heat to a nucleic acid such as a DNA but giving vibration to a nucleic acid solution may denature double strand nucleic acids such as a DNA to single strand nucleic acids.

In other words, another embodiment of the present invention is a method for denaturing double strand nucleic acids to single strand nucleic acids, including the denaturation step of giving the vibration that occurs in the vibration generation part 10 to a nucleic acid solution containing the double strand nucleic acids, thereby denaturing the double strand nucleic acids in the nucleic acid solution to the single strand nucleic acids.

Although the mechanism that vibration denatures double strand nucleic acids to single strand nucleic acids is not detailed, it is assumed that the vibrational energy from the outside breaks the hydrogen bonding between nucleic acids, thereby denaturing the double strand nucleic acids to the single strand nucleic acids.

When the nucleic acid is later amplified by a PCR method or the like, four kinds of deoxynucleoside triphosphates (dATP, dGTP, dCTP, dTTP), a primer pair, a DNA polymerase and the like, which are required for amplification of the nucleic acid, may be contained in the above described solution.

The above described denaturation step may be carried out with the use of the above described nucleic acid denaturation apparatus 100.

As described above, in accordance with the nucleic acid denaturation apparatus and the method for denaturing nucleic acids according to this embodiment, giving the vibration that occurs in the vibration generation part 10 to a nucleic acid solution containing double strand nucleic acids, thereby denaturing the double strand nucleic acids in the nucleic acid solution to single strand nucleic acids.

Because the denaturation by vibration is very simple and easy, and the sample environment is not severe, the denaturation by vibration may denature double strand nucleic acids to single strand nucleic acids, without various limitations by a conventional thermal or alkali denaturation. Accordingly, the denaturation by vibration may be widely used for an application to hybridization, a combination with a PCR or the like, and may also be expected to an application to local gene amplification in a living cell or a living body or the like, with the result that it is considered that the denaturation by vibration may contribute to elucidation of the gene expression mechanism.

The present invention is not limited only to the above described embodiments, but various kinds of modifications are possible in the claims.

Figure 6:
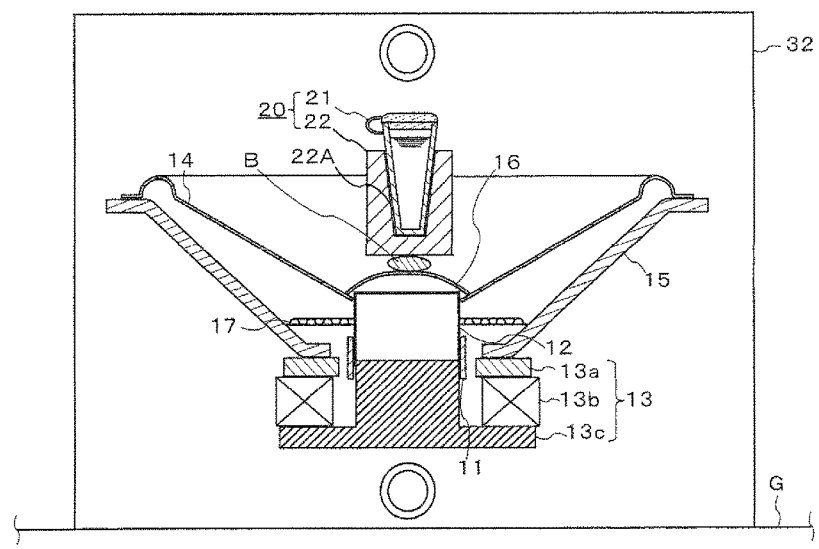
FIG. 6 is a cross sectional view of the position passing through the axis of a vibration board of a speaker, showing a modified example as to the connection of a vibration generation part to a container retainer member.

FIG. 6 is a cross sectional view of the position passing through the axis of the vibration board of the speaker, showing a modified example as to the connection of the vibration generation part to the container retainer member. A description has been made of the embodiment in which, as shown in FIG. 2 or 4, the container retainer member 22 is placed so as to place the vibration board 14 of the vibration generation part 10 in the horizontal direction with respect to the ground G, and in this state gives the vibration to the portion of the vibration board 14 or the cap 16, and through the container retainer member 22 to a nucleic acid solution received in the container 21. However, the present invention is not limited thereto.

The vibration board 14 may also be composed such that the vibration board 14 is placed so as to face in the vertical direction with respect to the ground G as shown in FIG. 6 to give the vibration to a nucleic acid solution.

In addition, the single strand nucleic acid as obtained above may be used in various kinds of applications.

In one embodiment, with the use of the above described single strand nucleic acid, double strand nucleic acids may be amplified by PCR. In other words, another preferable embodiment of the present invention is a method for amplifying nucleic acids including a step (1) of giving the vibration that occurs in the vibration generation part to a nucleic acid solution containing double strand nucleic acids, thereby denaturing the double strand nucleic acids to single strand nucleic acids, and a step (2) of amplifying double strand nucleic acids with the use of the single strand nucleic acid as a template.

A description of the step (1) is omitted here because it has been made above.

Instead of the step of dissociating double strand nucleic acids into single strand nucleic acids by thermal denaturation in a conventional PCR method or LCR method, in the present invention, the above described step (1) is used. Accordingly, as a method for amplifying nucleic acids, the steps in a conventional PCR method and LCR method other than the step of thermal denaturation may be used for double strand nucleic acid amplification.

As described above, in accordance with the denaturing method of the present invention, it is not necessary to use a heat-resistant DNA polymerase like denaturation by heat, which is expensive and has an inferior proofreading function. In addition, it is not always necessary to carry out temperature denaturation like a temperature fluctuation type PCR method, but it is possible to amplify nucleic acids at a constant temperature. Furthermore, it is not necessary in each step to add an alkali denaturation liquid, a neutralization liquid and a DNA polymerase like denaturation by alkali, but it is possible to carry out denaturation, annealing and elongation after preparation of a sample solution. Accordingly, the method for amplifying nucleic acids of the present invention may very easily amplify nucleic acids.

When nucleic acids are amplified by a PCR method or the like, in the step (1), various reagents required for latter double strand nucleic acid amplification may be contained in a sample to be denatured to single strands. The reagents required for the nucleic acid amplification include four kinds of deoxynucleoside triphosphates (dATP, dGTP, dCTP, dTTP), a primer pair, a DNA polymerase, a buffer solution and the like.

As a double strand nucleic acid amplifying method, there are two methods each carried out under a corresponding isothermal condition and a temperature variable condition, respectively, and the present invention may be carried out by either of these techniques. In the present invention, because the double strand nucleic acid amplification may be carried out even under an isothermal condition, in view of the simpleness of manipulation, it is preferable to carry out the amplification under an isothermal condition.

The isothermal condition means a condition where the environmental temperature in which the container for PCR reaction containing a PCR reaction solution is placed is controlled so as to be constant in each step, but the temperature of the PCR reaction solution itself is not necessary tube strictly constant. In addition, the isotherm is not necessary to be strictly the same temperature, but for example, refers to a temperature at which manipulation is carried out within the constant range. For example, the optimal temperature of a DNA polymerase having an excellent proof-reading function is usually not so high that the temperature is preferably from 10 to 42° C.

Note that in view of the simpleness of manipulation, it is preferable to carry out manipulation under an isotherm condition also in the step (1).

In addition, the available DNA polymerase is not limited, but includes a Pol I type enzyme represented by Taq polymerase, EX-Taq, LA-Taq, Expand series, Platinum series, Tbr, Tfl, Tru, Tth, Tli, Tac, Tne, Tma, Tih, Tfi and the like, a type enzyme represented by a Pfu, Pfu turbo, Pyrobest, Pwo, NOD, Bst, Sac, Sso, Poc, Pab, Mth, Pho, ES4, VENT and DEEP VENT, Bca (exo-) DNA polymerase, Klenow fragment of *E. coli* DNA polymerase I, Vent DNA polymerase, Vent (Exo-) DNA polymerase (Vent DNA polymerase from which the exonuclease activity is eliminated), Deep Vent DNA polymerase, Deep vent (Exo-) DNA polymerase (Deep Vent DNA polymerase from which the exonuclease activity is eliminated), φ29 phage DNA polymerase, MS-2 phage DNA polymerase Z-Taq DNA polymerase, or the like. These may be used alone or a plurality thereof may be used in combination. As these DNA polymerases, commercially available ones may be used.

In addition, a detection of nucleic acids amplified product may be carried out by dyeing with ethidium bromide a nucleic acid amplified product after agarose gel electrophoresis, or amplifying nucleic acids in the presence of a fluorescent intercalator, and subsequently irradiating the nucleic acid amplified product with UV. In addition, a quantitative Real-Time PCR method may provide quantitative analysis.

In addition, in preparing single strand nucleic acids for use with nucleic acid hybridization between single strands, the method for dissociation to single strands according to the present invention may also be used. In general, the nucleic acid hybridization reaction refers to a Southern hybridization, Northern hybridization or the like.

EXAMPLES

Hereinafter, a description is made of Examples and Comparative Examples. However, the technical scope of the present invention is not limited only to the following Examples.

(1) Example 1: Denaturation of Double Strand Nucleic Acid

Next, with the use of the nucleic acid denaturation apparatus shown in FIG. 6, an experiment to confirm denaturation of double strand nucleic acids was carried out.

With the use of Dneasy Plant Mini Kit (made by QIAGEN N.V.), 100 ng/µL of genomic DNA was extracted from *Arabidopsis thaliana*.

Into a 0.1 ml microtube (made by BIOplastics BV, model number BPB77201) was added 0.1 µl of the obtained genomic DNA, which was then diluted with 9.9 µl of Tris-EDTA buffer (TE), so that a DNA dilution was obtained. Subsequently, to the DNA dilution was added 1 µl of loading buffer (made by Takara Bio Inc., 6× Loading Buffer). In this way, 11 samples were prepared.

Moreover, in a state where the vibration in the vertical direction from the vibration board was transmitted to a nucleic acid solution that was the sample, 11 patterns of vibrations having 100 to 1,000 Hz and no vibration were applied to the corresponding nucleic acid solution at an amplitude of 0.5 mm for 120 seconds. The obtained sample was electrophoresed with 1% of agarose gel, and then dyed with SYBR (registered trademark) Green I (made by Takara Bio Inc.) capable of detecting a dsDNA and with SYBR (registered trademark) Green II (made by Takara Bio Inc.) capable of detecting an ssDNA. The applied voltage for electrophoresis is DC 100 V.

Figure 7:
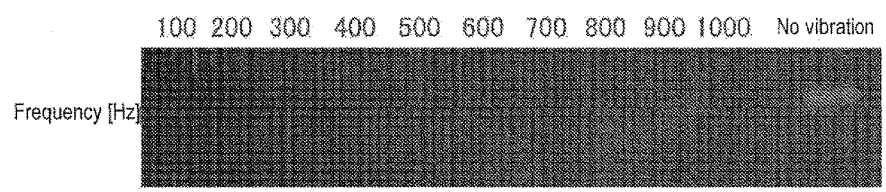
FIG. 7 is an electrophoretic pattern showing experimental results where a nucleic acid denaturation apparatus according to the present invention is used to add vibration to double strand DNAs and dyeing with SYBR Green is carried out.
Figure 8:
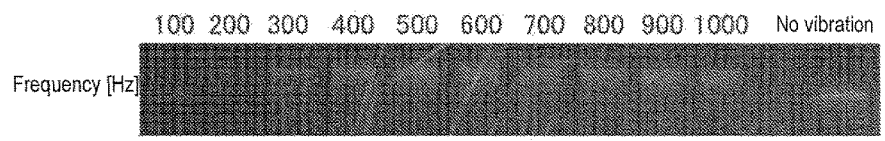
FIG. 8 is an electrophoretic pattern showing experimental results where the same apparatus is used to add vibration to double strand DNAs and dyeing with SYBR Green II is carried out.

FIG. 7 is an electrophoretic pattern showing experimental results where the nucleic acid denaturation apparatus according to the present invention was used and dyeing with SYBR Green I was carried out, and FIG. 8 is an electrophoretic pattern showing experimental results where the same apparatus was used and dyeing with SYBR Green II was carried out. In either of FIGS. 7 and 8, experimental results are displayed as Examples where the vibration has been applied having a corresponding frequency of 100, 200, 300 to 1,000 Hz increased by 100 Hz from the leftmost lane in the picture, and an experimental result is displayed at the rightmost lane as a Comparative Example where no vibration has been applied.

In FIG. 7, the line portion in the graph appears when SYBR Green I that is an indicator used reacts to a double strand DNA. When the line portion does not appear by SYBR Green I, but the line portion appears by SYBR Green II, it may be confirmed that double strand DNAs denatures to single strand DNAs.

In FIG. 7, the line displayed when no vibration has been added shows that double strand DNAs remains. On the other hand, the fluorescence disappears in the samples to which the vibration having a corresponding frequency of 100 to 1,000 Hz has been added. From these results, it may be confirmed that adding vibration denatures double strand DNAs to single strand DNAs.

In addition, in accordance with FIG. 8, although there is a difference in intensity, it may be confirmed that the line portion is sufficiently visually recognized. Taking these into consideration, it is considered that adding the vibration having a frequency of 100 to 1,000 Hz allows double strand DNAs to denature to single strand DNAs.

In this way, it has been confirmed that adding vibration to a nucleic acid solution without adding heat allows double strand DNAs to denature to single strand DNAs.

(2) Example 2: Double Strand Nucleic Acid Amplification by PCR Method

A reaction liquid was prepared as follows.

TABLE 1

10 × Klenow Fragment Buffer (made by Takara Bio Inc.) 5 µl
dNTP Mixture (made by Takara Bio Inc.) 4 µl
(a final concentration for each liquid of 200 µM)
Control Primer (Control Primer A: SEQ ID NO: 1,
Control Primer B: SEQ ID NO: 2) 0.5 µl each
(a final concentration for each liquid of 0.2 µM)
Klenow Fragment (made by Takara Bio Inc.) 1 µM
(a final concentration for liquid of 2 units/µl)
λ DNA (a template DNA, made by Takara Bio Inc.) 0.5 µM
(a final concentration for liquid of 0.5 ng/50 µl)
H$_2$O 38.5 µl
Total 50 µl The sequence of SEQ ID NO: 1 is 5'-GATGAGTTCGT-GTGCGTACAACT-3', and the sequence of SEQ ID NO: 2 is 5'-GGTTATCGAAATCAGCCACAGCGCC-3'.

In a 0.1 ml microtube (made by BIOplastics BV, model number BPB77201) was placed 15 µl of the above described reaction liquid as a sample.

Figure 9:
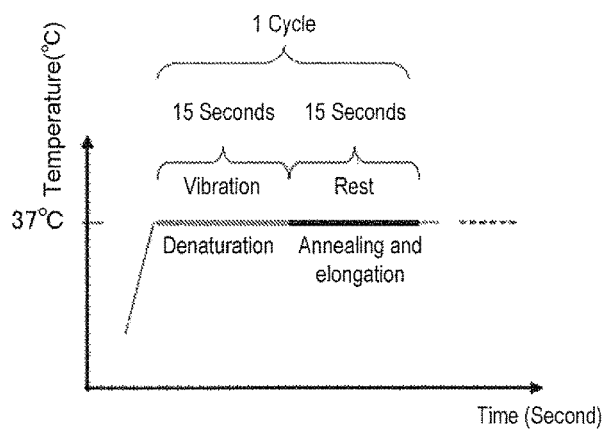
FIG. 9 is a diagram showing a cycle in double strand DNA amplification by a PCR method.
Figure 10:
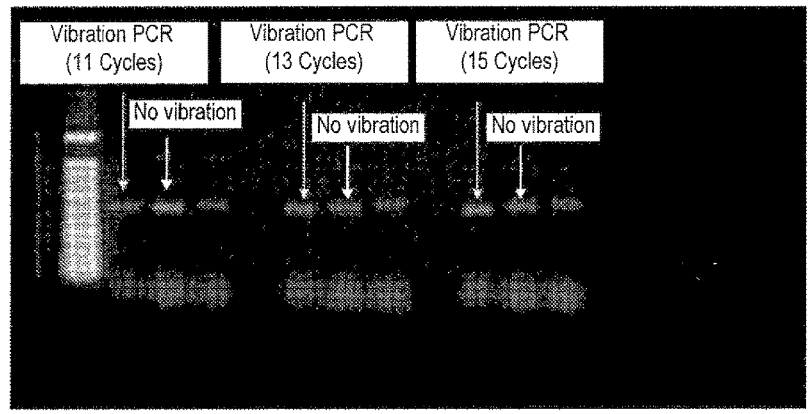
FIG. 10 is an electrophoretic pattern showing experimental results where a PCR method is carried out with the use of a nucleic acid denaturation apparatus according to the present invention.

Subsequently, with the use of the apparatus in FIG. 6, in a state where the vibration in the vertical direction from the vibration board was transmitted to a nucleic acid solution that was the sample, the vibration was given at 130 Hz (wave-shaped sine wave) for 15 seconds, and then the rest was taken for 15 seconds. With the vibration for 15 seconds and the rest for 15 seconds as one cycle, experiments were carried out for 11, 13, and 15 cycles (FIG. 9). Accordingly, the total time will be 30 seconds×the number of cycles. In each case, the experiment was carried out such that the temperature was maintained at a constant temperature of 37° C. On the other hand, as a comparison, the same experiment as those for the above described Examples was carried out, except that the vibration was not given at all, but only the temperature was maintained at a constant temperature of 37° C. The retention time corresponded to the above described total time. The electrophoretic result is shown in FIG. 10. In FIG. 10, the one to which the cycles including the vibration and the rest has been applied is represented as "vibration PCR", and the one to which the vibration has not given at all is as "no vibration".

In accordance with the result in FIG. 10, when the number of cycles is 11, the brightness of the band from the vibration PCR is darker than that from no vibration, but when the number of cycles is 13, the brightness is at the same level as each other, and further when the number of cycles is 15, the band from the vibration PCR is deeper than that from no vibration. From these facts, it is found that a DNA is amplified more as the number of cycles increases.

This application is based on JP-2012-189441 A filed on Aug. 30, 2012, the disclosure of which is hereby incorporated by reference in its entirety.

REFERENCE SIGNS LIST

10: Vibration generation part
11: Voice coil
12: Voice coil bobbin
13: Magnetic circuit
13A: Plate
13E: Magnet
13C: Yoke
14: Vibration board
14A: Vibrator
15: Frame
16: Cap
17: Damper
100: Nucleic acid denaturation apparatus
20: Nucleic acid solution reception part
21: Container
22: Container retainer member
22A: Reception part
31, 32: Plastic boards
33, 34: Bolts
41: Support board
41A: Container insertion hole
42: Fixing board
A: Vibration direction (horizontal to ground)
B: Adhesive
G: Ground

The invention claimed is:

1. A nucleic acid denaturation apparatus, comprising:
a vibration generation part including a vibration board, the vibration board being adapted to generate vibration to be given to a nucleic acid solution containing double strand nucleic acids;
a nucleic acid solution reception part including a container to receive the nucleic acid solution; and
a vibration transmission member for transmitting the vibration from the vibration board to the nucleic acid solution reception part, the vibration transmission member consisting of an inverted L-shaped support board wherein the inverted L-shaped support board comprises a downwardly extending leg and a horizontally extending arm, and wherein the downwardly extending leg is connected to the vibration generation part and the horizontally extending arm defines an insertion hole for receiving the container of the nucleic acid solution reception part;
wherein the insertion hole is positioned in the horizontally extending arm of the inverted L-shaped support board so as to place the nucleic acid solution reception part away from the vibration board, the vibration generation part conveys the vibration from the vibration board in a direction transverse to the downwardly extending leg and, through the vibration transmission member, the vibration is imparted to the nucleic acid solution in the nucleic acid solution reception part by the horizontally extending arm in a direction along a length of the horizontally extending arm, which causes the double strand nucleic acids in the nucleic acid solution to denature to single strand nucleic acids.

2. The nucleic acid denaturation apparatus according to claim 1, wherein the vibration generation part generates the vibration in audible range.

3. The nucleic acid denaturation apparatus according to claim 2, wherein a frequency in the audible range is from 20 Hz to 20,000 Hz.

4. The nucleic acid denaturation apparatus according to claim 1, wherein the nucleic acid solution reception part further comprises a container retainer member for retaining the container freely attachably and detachably.

5. The nucleic acid denaturation apparatus according to claim 4, wherein the container retainer member comprises a detachment prevention mechanism for preventing the container from being detached when the vibration from the vibration board is given.

6. The nucleic acid denaturation apparatus according to claim 1, wherein the vibration transmission member holds the nucleic acid solution reception part at a position extending vertically and horizontally away from the vibration generation part.

7. A method for denaturing nucleic acids in solution, comprising a step of imparting vibration that occurs in a vibration generation part of the nucleic acid denaturation apparatus of claim 1 to a container containing nucleic acid solution containing double stranded nucleic acids, and denaturing the double strand nucleic acids in the nucleic acid solution to single strand nucleic acids.

8. The method for denaturing nucleic acids according to claim 7, wherein the vibration is a vibration in audible range.

9. The method for denaturing nucleic acids according to claim 8, wherein a frequency within the audible range is from 20 Hz to 20,000 Hz.

10. The method of claim 7, further comprising amplifying the single strand nucleic acids.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence -continued

```
<220> FEATURE:
<223> OTHER INFORMATION: primer

<400> SEQUENCE: 1
gatgagttcg tgtccgtaca act                                          23

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
ggttatcgaa atcagccaca gcgcc                                        25
```